United States Patent [19]

Junghans

[11] Patent Number: 4,565,657

[45] Date of Patent: Jan. 21, 1986

[54] PROCESS FOR THE PRODUCTION OF 17α-ACYLOXY-6-CHLORO-1α,2α-METHYLENE-3,20-DIONES

[75] Inventor: Klaus Junghans, Berlin, Fed. Rep. of Germany

[73] Assignee: Schering Aktiengesellschaft, Berlin and Bergkamen, Fed. Rep. of Germany

[21] Appl. No.: 647,211

[22] Filed: Sep. 4, 1984

[30] Foreign Application Priority Data

Sep. 1, 1983 [DE] Fed. Rep. of Germany ....... 3331824

[51] Int. Cl.[4] ................................................ C07J 1/00
[52] U.S. Cl. ......................... 260/397.4; 260/239.55 R
[58] Field of Search ..................................... 260/397.4

[56] References Cited

U.S. PATENT DOCUMENTS 3,234,093  2/1966  Wiechert ........................ 260/397.4
4,457,925  7/1984  Bittler et al. ............... 260/239.55 C Primary Examiner—Elbert L. Roberts
Attorney, Agent, or Firm—Millen & White

[57] ABSTRACT

A process for the production of 17α-acyloxy-6-chloro-1α,2α-methylene-3,20-diones of the general Formula I

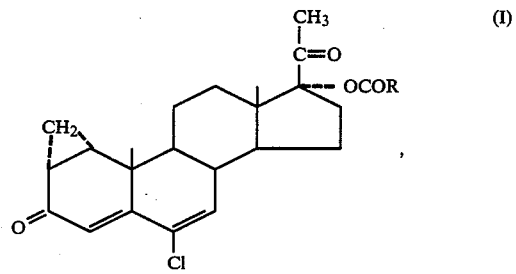

wherein R represents an alkyl group with up to 5 carbon atoms or a phenyl group, is characterized in that a compound of general Formula II

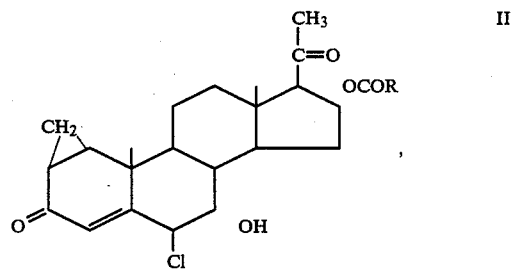

wherein R has the meaning indicated above, is reacted, in the presence of a strong acid, with a compound of general formula III

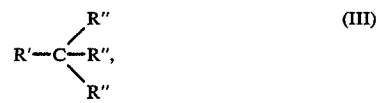

wherein R' is a hydrogen atom or an alkyl group with up to 4 carbon atoms and R" represents alkoxy groups, alkylthio groups or dialkylamino groups with 1 to 4 carbon atoms in each alkyl radical.

12 Claims, No Drawings

PROCESS FOR THE PRODUCTION OF 17α-ACYLOXY-6-CHLORO-1α,2α-METHYLENE-3,20-DIONES

BACKGROUND OF THE INVENTION

This invention relates to a process for preparing 17α-acyloxy-6-chloro-1α,2α-methylene-3,20-diones.

It is known that such compounds (i.e., those of Formula I below) are valuable pharmaceutical agents. (See, e.g., U.S. Pat. No. 3,234,093.) The compound of Formula I below with R as a methyl group (=cyproterone acetate) is used as an active ingredient in commercial drugs.

Synthesis of these compounds is quite expensive and the yields achieved are unsatisfactory.

SUMMARY OF THE INVENTION

Accordingly, it is an object of the invention to provide an improved process for preparing such compounds.

Upon further study of the specification and appended claims, further objects and advantages of this invention will become apparent to those skilled in the art.

These objects have been achieved by providing a process for the production of 17α-acyloxy-6-chloro-1α,2α-methylene-3,20-diones of Formula I

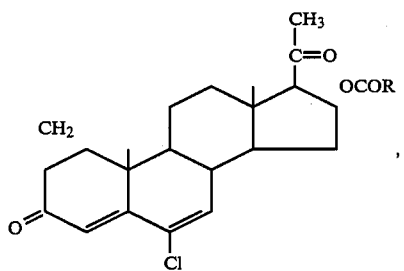

wherein R represents an alkyl group of up to 5 carbon atoms or a phenyl group,
comprising reacting a compound of Formula II

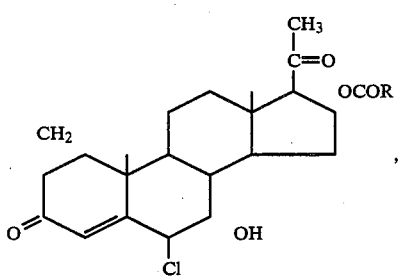

wherein R is as defined above,
in the presence of a strong acid, with a compound of Formula III

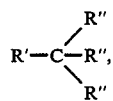

wherein R' is a hydrogen atom or an alkyl group of up to 4 carbon atoms and R" represents alkoxy groups, alkylthio groups or dialkylamino groups or combinations thereof with 1 to 4 carbon atoms in each alkyl radical.

DETAILED DISCUSSION

It has now been found that in a surprising way the mentioned compounds can be synthesized by the process according to this invention in a notably simpler way, while achieving significantly more favorable yields.

The compounds of Formula III that are necessary for the process according to the invention are predominantly ortho esters of a carboxylic acid with up to 4 carbon atoms, preferably acetic acid, ortho esters of formic acid, ortho esters of thioacetic acid or dimethylformamide dialkylketals. These are known compounds. Dimethyl esters and diethyl esters are preferably used as the alcohol components of the ortho esters, i.e., R" preferably has $C_{1-2}$-alkyl groups. Trimethyl orthoformate, triethyl orthoformate, trimethyl orthoacetate, triethyl orthoacetate, dimethylformamide dimethylketal or dimethylformamide diethylketal are used particularly as compounds of Formula III.

These substances are used either as the sole solvents for the reaction or preferably in combination with other inert solvents in a ratio of about one mole per mole of compound of Formula II. Suitable inert solvents include, for example, chlorinated hydrocarbons such as dichloromethane, trichloromethane, tetrachloroethylene or trichloroethylene, ethers such as diethyl ether, diisobutyl ether, glycol dimethyl ether, dioxane or tetrahydrofuran, dipolar aprotic solvents such as dimethylformamide or hexamethylphosphoric triamide or aromatic, liquid hydrocarbons such as benzene, toluene, xylenes, etc.

The reaction is performed in the presence of strong acids, which are preferably used in catalytic amounts (e.g., about 0.01 to 0.2 mole per mole of steroid). Suitable pKa's of the acids are equal to or less than 3.5.

Suitable acids are, for example, inorganic acids such as sulfuric acid, anhydrous hydrochloric acid and perchloric acid, alkylsulfonic acids such as methanesulfonic acid, arylsulfonic acids such as p-toluenesulfonic acid, trichloromethylacetic acid, trifluoromethylacetic acid or strongly acidic ion exchangers such as Amberlite®IR 120. Other equivalent acidic reagents are readily recognized.

The reaction is preferably performed at 0° to 100° C., most simply the reaction occurring at room temperature. Typical reaction times are usually 1–12 hours.

The starting compounds of Formula II can be produced from the corresponding 6α,7α-epoxides in a simple way by means of dilute hydrochloric acid, as the following production method exemplifies:

10.0 g of 17α-acetoxy-6α,7α-epoxy-1α,2α-methylene-4-pregnene-3,20-dione is mixed with 50 ml of tetrahydrofuran and 25 ml of dilute hydrochloric acid (8 ml conc. hydrochloric acid and 17 ml of water) and stirred for 15 minutes at room temperature. Then, 200 ml of water is added to the reaction mixture; extraction is performed with dichloromethane, and the organic phase is dried with magnesium sulfate, concentrated in vacuo, and 10.8 g of 17α-acetoxy-6β-chloro-7α-hydroxy-1α,2α-methylene-4-pregnene-3,20-dione with a melting point of 154°–156° C. is obtained.

The 6α,7α-epoxides are known and readily preparable using conventional methods from known starting materials. See, e.g., U.S. Pat. No. 3,439,093.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

5.0 g of 17α-acetoxy-6β-chloro-7α-hydroxy-1α,2α-methylene-4-pregnene-3,20-dione is mixed in 25 ml of dichloromethane with 0.1 g of p-toluenesulfonic acid and 3.0 ml of trimethyl orthoformate. The mixture is allowed to stand for 4 hours at 0° C., mixed with 20 ml of water and stirred for 15 minutes. Then the organic phase is separated, dried with sodium sulfate and concentrated in vacuo. Thus, 4.8 g of 17α-acetoxy-6-chloro-1α,2α-methylene-4,6-pregnadiene-3,20-dione with a melting point of 202° to 205° C. (80% purity) is obtained.

EXAMPLE 2

5.0 g of 17α-acetoxy-6β-chloro-7α-hydroxy-1α,2α-methylene-4-pregnene-3,20-dione is mixed in 90 ml of toluene with 0.2 g of p-toluenesulfonic acid and 5.0 ml of triethyl orthoacetate and kept for 6 hours at room temperature. The reaction mixture is worked up as described in Example 1 and 4.6 g of 17α-acetoxy-6-chloro-1α,2α-methylene-4,6-pregnadiene-3,20-dione with a melting point of 200° to 202° C. (78% purity) is obtained.

EXAMPLE 3

5.0 g of 17α-acetoxy-6β-chloro-7α-hydroxy-1α,2α-methylene-4-pregnene-3,20-dione is mixed in 60 ml of tetrahydrofuran with 0.15 ml of methanesulfonic acid and 3.0 ml of dimethylformamide diethylketal. The reaction mixture is allowed to stand for 3.5 hours, mixed with 150 ml of water, extracted with dichloromethane, the organic phase is dried with magnesium sulfate, concentrated in vacuo and 4.7 g of 17α-acetoxy-6-chloro-1α,2α-methylene-4,6-pregnadiene-3,20-dione with a melting point of 201° to 204° C. (80% purity) is obtained.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the production of a 17α-acyloxy-6-chloro-1α,2α-methylene-3,20-dione of the formula

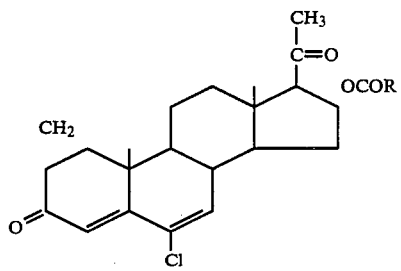

wherein R is alkyl of up to 5 carbon atoms or phenyl comprising reacting a compound of the formula

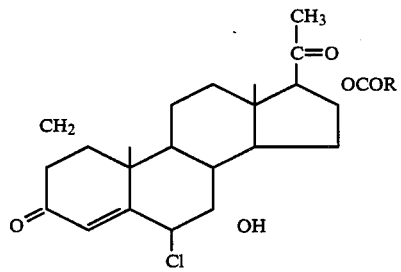

wherein R is as defined above, in the presence of a strong acid, with a compound of the formula

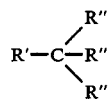

wherein R' is hydrogen or alkyl of up to 4 carbon atoms and R" represents alkoxy groups, alkylthio groups, dialkylamino groups or a combination thereof, with 1 to 4 carbon atoms in each alkyl radical.

2. A process of claim 1 wherein R is methyl.
3. A process of claim 1 wherein R is ethyl.
4. A process of claim 1 wherein R" represents a methoxy or ethoxy group.
5. A process of claim 1 wherein the compound having R" groups is an ortho ester of acetic acid, formic acid or thioacetic acid or is a dimethylformamide dialkylketal.
6. A process of claim 1 wherein the compound having R" groups is trimethyl orthoformate, triethyl orthoformate, trimethyl orthoacetate, triethyl orthoacetate, dimethylformamide dimethylketal or dimethylformamide diethylketal.
7. A process of claim 1 wherein the amount of compound containing R" groups is about one mole per mole of starting steroid.
8. A process of claim 1 conducted in the presence of an inert, reaction compatible solvent.
9. A process of claim 1 wherein the amount of strong acid is 0.01 to 0.2 mole per mole of starting steroid.
10. A process of claim 1 wherein the strong acid is sulfuric acid, anhydrous hydrochloric acid, perchloric acid, an alkylsulfonci acid, an arylsulfonic acid, trichloromethylacetic acid, trifluoromethylacetic acid or a strong acidic ion exchanger.
11. A process of claim 1 carried out at a temperature of 0°-100° C.
12. A process of claim 11 carried out at about room temperature.

* * * * *